United States Patent [19]

Raible

[11] 4,428,934
[45] Jan. 31, 1984

[54] METHOD FOR OXYGENATING BLOOD

[75] Inventor: Donald A. Raible, Santa Ana, Calif.

[73] Assignee: Bentley Laboratories, Inc., Irvine, Calif.

[21] Appl. No.: 288,118

[22] Filed: Jul. 29, 1981

Related U.S. Application Data

[60] Division of Ser. No. 823,149, Aug. 9, 1977, Pat. No. 4,282,180, which is a continuation-in-part of Ser. No. 689,971, May 26, 1976, Pat. No. 4,268,476, which is a continuation-in-part of Ser. No. 584,464, Jun. 6, 1975, abandoned.

[51] Int. Cl.$^3$ ............................................ A61K 35/14
[52] U.S. Cl. ..................................... 424/101; 422/45; 435/2
[58] Field of Search .............. 424/101; 435/2; 422/45, 422/46, 47

[56] References Cited

U.S. PATENT DOCUMENTS 4,138,288  2/1979  Lewin ..................................... 435/2

*Primary Examiner*—Sam Rosen
*Attorney, Agent, or Firm*—Lyon & Lyon

[57] ABSTRACT

A rigid blood oxygenator in which blood and oxygen-rich gas are admitted at the top of the device and caused to flow substantially concurrently downwardly through a tortuous path. During the course of this downward flow, oxygen-rich gas bubbles are formed in the blood and a gas transfer is accomplished according to which the oxygen content of the blood is enriched and carbon dioxide is removed from the blood, which gas transfer is enhanced by the secondary flow induced by the tortuous path. During the course of downward flow, the blood-gas-bubble mixture is also passed around a heat exchange device, which preferably is convoluted so as to form a tortuous path, to bring the blood to a desired temperature. The device is equipped with a defoaming means such that the blood bubbles are converted back into liquid blood, which is then returned to the patient. Vent means are provided for removal of carbon dioxide and other vent gases. Means for promoting secondary flow in the blood are preferably provided in the upward region of the oxygenator. The present invention also comprehends the method of transferring gas in which the flow path of the blood-gas mixture during oxygenation is in a substantially downward direction and is tortuous, as well as simultaneous causing heat exchange to occur.

20 Claims, 5 Drawing Figures

METHOD FOR OXYGENATING BLOOD

RELATED APPLICATIONS

This application is a division of my copending application Ser. No. 823,149 filed Aug. 9, 1977 (now U.S. Pat. No. 4,282,180), which in turn is a continuation-in-part of my application Ser. No. 689,971 filed May 26, 1976 (now U.S. Pat. No. 4,268,476), which is a continuation-in-part of my application Ser. No. 584,464 filed June 6, 1975 (now abandoned), each of which is incorporated by reference herein.

BACKGROUND OF THE INVENTION

The present invention relates to a blood oxygenator and to a method for oxygenating blood.

The history of safe and reliable blood oxygenators is relatively brief. Such oxygenators are used in open-heart surgery and other operations and treatments of the body when it is necessary to establish an extracorporeal circulation system for temporarily assuming the functions of the heart and lungs of the patient. In such a system, the oxygenator operates to perform the function usually performed by the lungs of the patient, i.e., the life-supporting transfer of oxygen into the blood and carbon dioxide out of the blood. The oxygenator is used in association with a pump which performs the function of the heart to cause circulation of the blood. Thus, early versions of the oxygenator were often referred to as "heart-lung" machines. The early heart-lung machines were typically rotating discs which passed through a pool of blood, but were only partially immersed therein such that the free surface of the disc exposed the blood to oxygen and accomplished some gas transfer. After this, bag-type oxygenators were introduced which were superior to the disc oxygenators, but which left much to be desired.

A major advance occurred in the mid-1960's when the rigid (or hard-shell) bubble oxygenator was developed. The history of such oxygenators had its beginnings in the device shown in Raible, et. al. U.S. Pat. No. 3,468,631 and they first came into clinical use with the development of the devices shown in Bentley, et. al. U.S. Pat. Nos. 3,488,158 and 3,578,411 which have come to be known as the Bentley Oxygenator. At the present time, such oxygenators are used more frequently than any other type. Among the important features of the oxygenators disclosed in the foregoing patents, the disclosures of which are incorporated herein by reference, was the provision of a self-contained heat exchanger.

In the intervening years, some relatively minor modifications have been made in bubble oxygenators, e.g., those disclosed in Brumfield U.S. Pat. Nos. 3,764,271 and 3,769,162. However, all rigid bubble oxygenators as shown in the aforesaid patents and all other such oxygenators known to applicant to have been put to actual clinical use have had one fundamental feature in common, namely, each of them introduced blood and oxygen-rich gas in the lower region of the device and caused a column of bubbles to flow upwardly through the initial portion of the device. Bentley, et. al. U.S. Pat. Nos. 3,488,158 and 3,578,411 and the aforesaid Brumfield Patents do have some downward portions in the flow path of the gas blood mixture, but it is clear that they were designed to provide for initial upward flow of the gas and blood mixture in that portion of the flow path where the bubbles are formed. In addition, Fields U.S. Pat. No. 3,204,631, discloses an oxygenator in which blood enters at an upper portion and oxygen enters at a lower portion such that there is a counter-flow relationship with the blood initially flowing downwardly and the oxygen flowing upwardly.

SUMMARY OF THE INVENTION

The oxygenator and method of the present invention depart from the design and mode of operation of previous rigid bubble oxygenators in that, in the present invention, the gas and blood enter the oxygenator at the top or upward region thereof and both follow a downward path through substantially the entire flow path through gas transfer portion of the oxygenator, which path contains means for inducing secondary flow and is referred to as "tortuous" herein. A heat exchange device is placed in this downward path to bring the blood to the desired temperature. In the preferred embodiment of the present invention, this heat exchange device is a helically wrapped convoluted tube through which a heat exchange fluid passes and around which the blood-gas mixture passes. In the preferred embodiment of the present invention, means for imparting secondary flow to the blood-gas mixture in the initial portion of its flow path is also provided. Surprisingly, it has been found that a very high degree of gas transfer efficiency is achieved when the device and method of the present invention employing generally downward flow are used. Defoaming means are provided to break the bubbles and to convert the blood bubbles to liquid form prior to return of the blood to the patient. A reservoir is provided at the lower end of the oxygenator and vent means for escape of carbon dioxide and other gas is provided at the upper end of the oxygenator. In the preferred embodiment of the oxygenator, the means for imparting secondary flow in the initial portion of the flow path comprises an undulating path which is generally conical in shape. These and other important features of the present invention are described in more detail in the following disclosure.

DESCRIPTION OF THE DRAWINGS

As shown in FIG. 1, in its preferred embodiment, the oxygenator of the present invention is generally cylindrical in configuration. The oxygenator comprises an outer shell 1 which is provided with a gas inlet 2 and blood inlets 3 and 4. Inlet 5 is provided for priming as well as for optimal medication administration and, if needed, as a return inlet from a cardiotomy reservoir. Blood outlets 6 and 7 and gas vent 9 are also provided. The inlet 10 for heat exchanger fluid and outlet 11 are also provided.

Referring to FIG. 3, the internal construction of the oxygenator is shown in more detail. As there depicted, gas inlet 2 connects with annular chamber 12 which is bounded on its upper end by diffusion means 13. This diffusion means may be any suitable porous or perforated apperturned member, but preferably is a perforated member. This perforated diffusion member does not constitute part of the present invention, but rather is a separate invention which is assigned to the assignee of the present application. In its prefered form the diffusion means has three circular patterns containing 66 perforations which are 0.010 inches in diameter and 6 perforations which are 0.025 inches in diameter, the larger perforations being more or less uniformly distributed among the smaller perforations.

Figure 1:
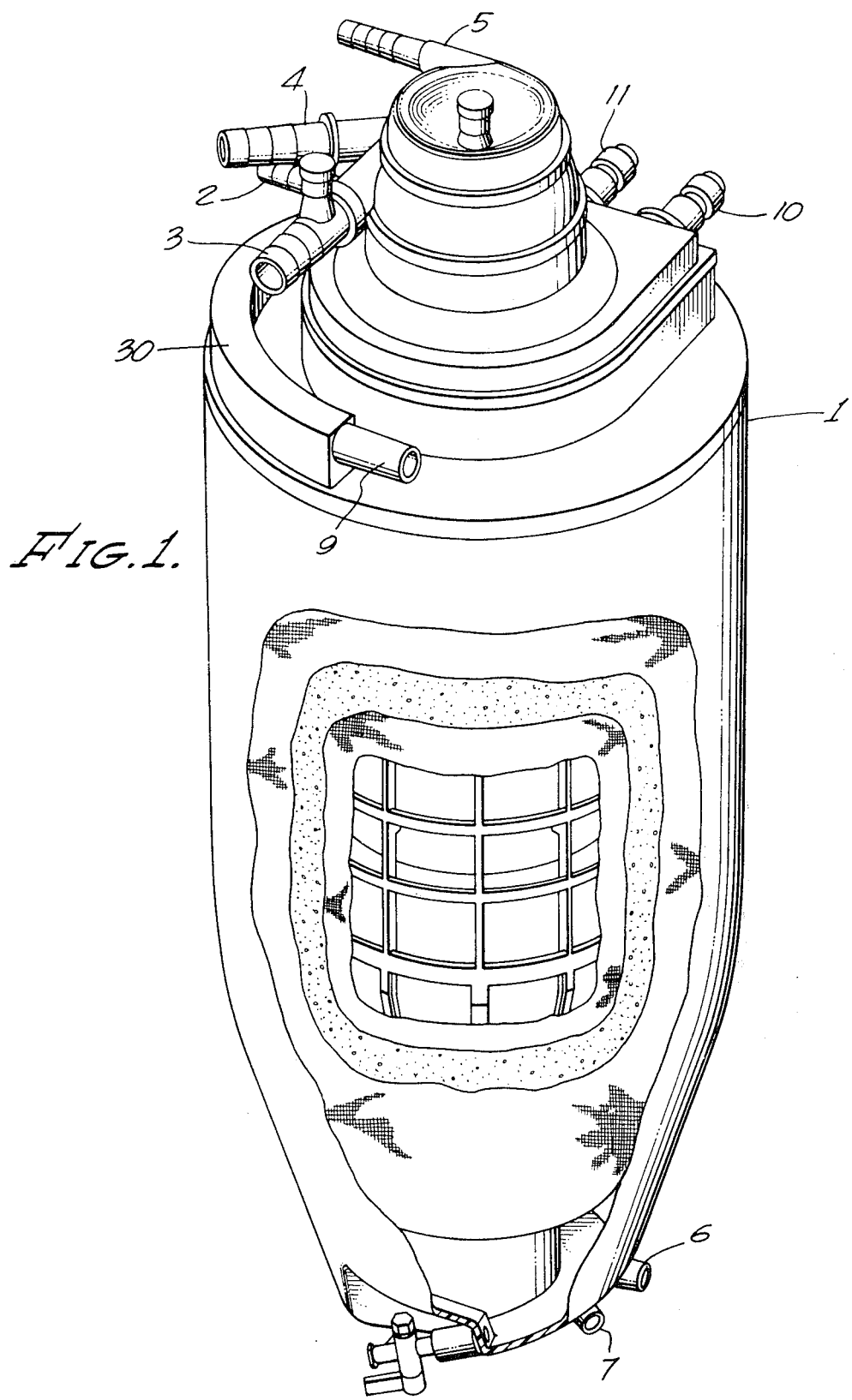
FIG. 1 is a perspective view of the oxygenator of the present invention.
Figure 2:
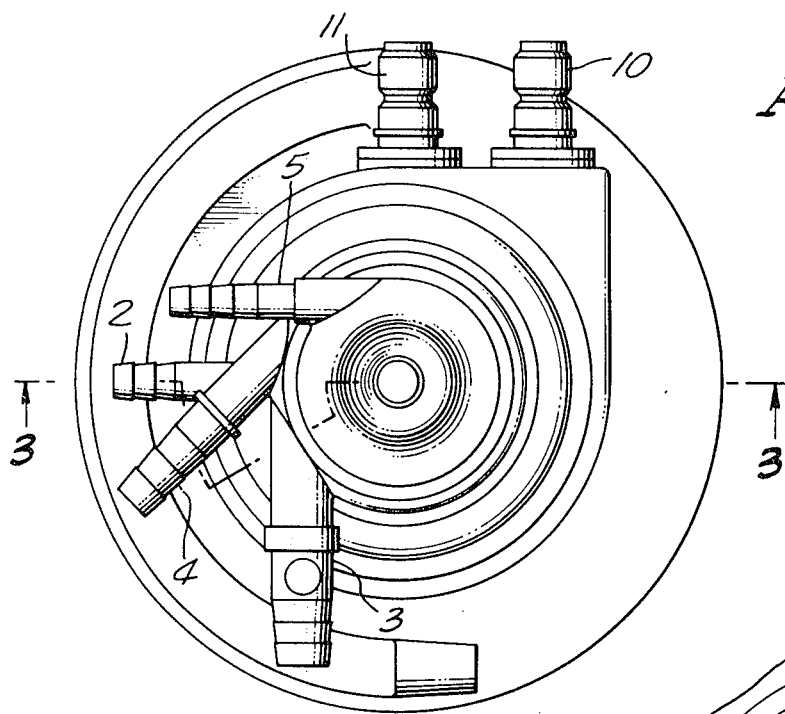
FIG. 2 is a top view of the oxygenator.

Blood inlet means 3 and 4 connect with the interior of annular chamber 14 in a generally tangential manner. Thus, when chamber 14 is filled with blood, flowing in a spiral manner, and gas is admitted to the device through inlet 2, the gas, such as oxygen or an oxygen-rich mixture, passes through inlet 2, into chamber 12 and through diffusion means 13 into the body of blood in chamber 14. As will be described in more detail below, bubbles are formed in chamber 14 when the gas enters the blood.

Chamber 14 connects with annular channel 15 and undulating distribution channel 16, the latter being conical in general shape. Channel 16 connects with annular mixing chamber 17 which is provided with heat exchange tubing 18. Heat exchange tubing 18 is a convoluted tubing having a large diameter portion 19 and a smaller diameter portion 20. Thus, although heat exchange tubing has a large diameter 19 which is essentially the same dimension as the radial distance between inner wall 21 and outer wall 22 of the mixing chamber, there are a plurality of flow paths between the walls of the mixing chamber and the walls of tubing 18 formed by the convolution. In addition, since tubing 18 is helically wrapped around inner wall 21, there is a helically descending flow path through the bubble column.

At the lower end of chamber 17, outer wall 22 terminates approximately two-thirds of the distance from the top to the bottom of the oxygenator to permit the bubbles of blood to come into contact with defoaming means 23. While several defoaming means may be used, e.g., that disclosed in U.S. Pat. No. 3,468,631, it is preferred in the present invention to form defoaming material 23 from a polyurethane foam having about ten to thirty pores per inch. The polyurethane foam is coated with a silicone defoaming agent. Optionally, a spacer 25 may be provided between defoaming material 23 and wall 22. Spacer 25 may comprise a ribbed structure which provides open spaces therebetween.

Open spaces 26 are provided in space 25 which permit blood to come into contact with defoaming material 23. The lower end of the oxygenator is provided with reservoir 29 where liquid blood is collected.

Annular passage 30 connects with vent means 9 so that vent gases may be exhausted from the oxygenator. A mesh sleeve 31 which may be polyester, polypropolene, polyethelene, nylon or other suitable fabric is positioned around defoaming material 23 and is provided with elastic bands 32 to hold it in place. Port 5 connects with chamber 35 which, in turn, connects with conduit 36. Port 5 is used for priming the oxygenator and may also be used for addition of medication to the blood or for blood coming from a cardiotomy reservoir.

Figure 4:
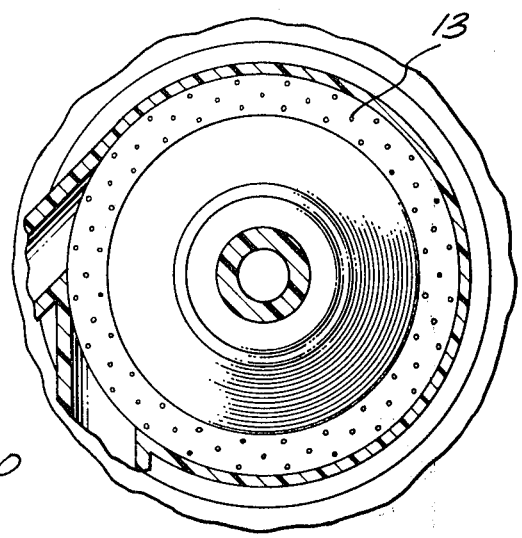
FIGS. 4 and 5 are transverse sections of the oxygenator.
Figure 5:
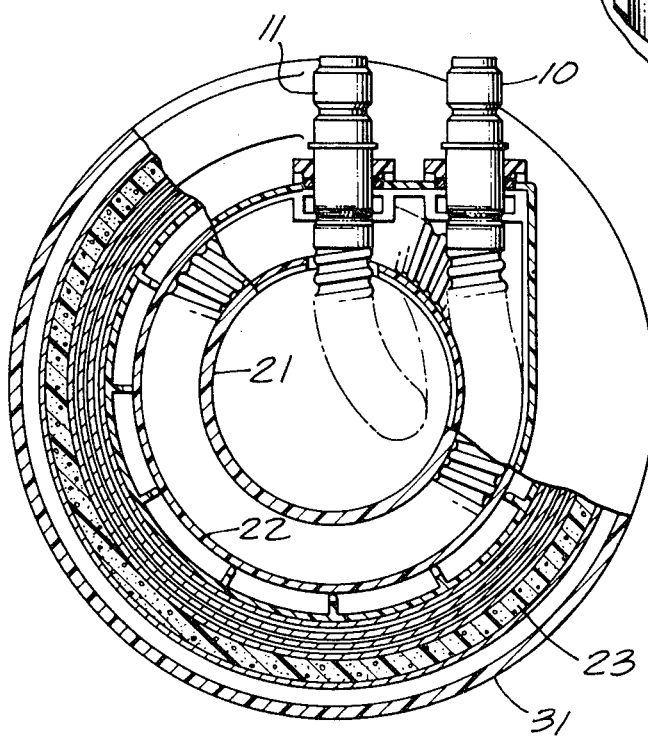
Figure 3:
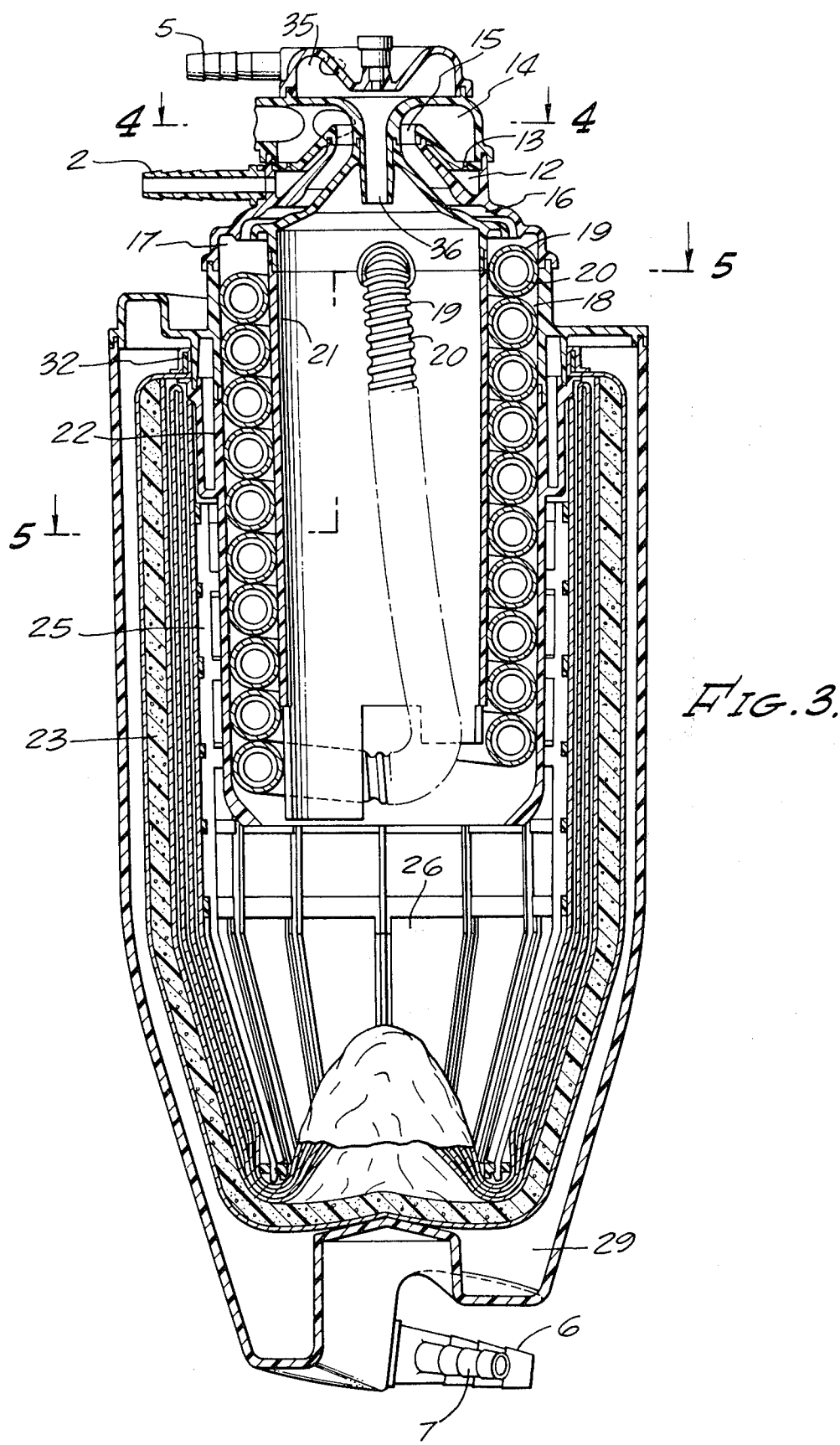
FIG. 3 is a cross sectional view of the oxygenator taken along its axis.

FIGS. 4 and 5 further illustrate the internal structure.

It is to be understood that the present invention is not to be limited to any particular theory of operation. However, in an effort to provide as complete a disclosure as possible of the mode of operation of the present invention, the description which follows is believed to be accurate on the basis of present information. Even if future information were to demonstrate that the understanding of the invention which presently exists is incomplete or inaccurate in some respect, one essential fact would remain unchanged, namely, the apparatus and method of the present invention achieve a significant step forward in blood oxygenation technology. The key feature of this forward step which results in increased efficiency both with regard to gas transfer during oxygenation and in heat exchange is the combination of the substantially concurrent downward flow path of the blood-gas mixture with the secondary flow which occurs in that path. In addition, the location of the heat exchange means in this downward path is of substantial significance.

The operation of the present invention will be described with reference to the specific embodiment shown in the drawings. After oxygen enters through port 2 and passes through passageway 12 and perforated member 13, it mixes with blood entering through ports 3 and 4 and the mixture flows in a spiral direction through chamber 14 and into passage 15 and then into conical passage 16 which has an undulating cross section. This undulating cross section promotes secondary flow and the bubbled blood is spread outwardly and down into bubble column 17 where it continues to flow downwardly through two primary flow paths. First, since heat exchanger tubing 18 is convoluted, there is a more or less vertically downward path through the convolutions. Second, there is a helically downward path generally parallel to the path defined by the helically coiled heat exchanger tubing. These primary flow paths are also influenced by the flow deflection caused by heat exchanger tubing 18 itself. Thus, the bubbled gas-blood mixture flows substantially downwardly, but is influenced by a variety of factors such that effective mixing of the gas with the blood is promoted by reason of repeated twists and turns in the downward path taken by the blood-gas mixture. It is believed that the bubbles are rotated as they follow this path and that they are caused to change shape from generally circular to elongated elliptical and back again.

In this regard, it should be noted that when the blood-gas mixture passes through conical chamber 16, there is some reduction in pressure from the top of the chamber 16 to near atmospheric pressure when discharged at the top of bubble column 17. Thus, the size of the bubbles in chamber 16 generally increases as the blood-gas mixture flows through that chamber.

Preferably, the external convolutions on the heat exchange tubing 18 are also present on its internal wall as well to promote turbulent flow of the fluid, e.g., water, passing through heat exchange tubing 18 to provide increased heat transfer efficiency. Furthermore, it is believed that as the blood bubble mixture flows over the convoluted heat exchanger tubing, a thin film of blood is caused to cover the surface of the tubing due to surface tension. As further supplies of bubbled-blood come into contact with the blood covering the heat exchanger tubing surface, the film becomes too thick and heavy to remain on the surface of the heat exchanger tubing and the now-warmed blood film runs from the surface of the convoluted tubing and is either re-bubbled with the free oxygen present or continues to run as a liquid down through the bubble column. Thus, a type of filming heat exchange is believed to take place in which the velocity components of gravitational flow and of the pressure exerted by the incoming blood-gas mixture are both in a downward direction and, hence, are additive. It is believed that this combination of circumstances, which is believed to be unique to the present invention, has a significant effect in increasing the efficiency of heat exchange in the present invention.

The mechanism of gas exchange in bubble oxygenators is the subject of several theories and it is entirely possible that different mechanisms predominate in different designs of bubble oxygenators. In the present invention, it is believed that when oxygen comes in contact with the incoming blood in chamber 14, oxygen bubbles are formed in blood and that these bubbles become covered with plasma and red cells. It is believed that the oxygen is then transferred through the membrane of the red cell and into the hemoglobin where biologic gas transfer takes place, such that oxygen enters the blood and carbon dioxide is released.

Thus, gas exchange is believed to be accomplished in conical chamber 16 and in mixing chamber 17 after which the blood bubbles flow through the defoamer material previously described. The oxygenated, defoamed liquid blood is then removed from the oxygenator and returned to the patient. Excess oxygen and carbon dioxide gases are vented upwardly and out of the top of the housing.

Among the important advantages of the present invention is the minimization and possible elimination of reverse blood flow, i.e., the phenomenon which occurs in all bubble oxygenators known to applicant in which upwardly traveling blood bubbles break and liquid blood flows downwardly back toward the point where oxygen is introduced such that some blood has a substantially longer residence time in the bubble column than other blood. Reverse flow is disadvantageous because the risk of blood damage by reason of repeated bubbling and breaking of the bubbles for an extended time exists and because the patient is deprived of a portion of his blood for a time longer than that required to accomplish oxygenation. Furthermore, the present invention permits zero retention of the patient's blood volume after the surgical procedure and requires a smaller amount of blood to be in the oxygenator at any given time. Similarly, the oxygenator of the present invention is less sensitive to variations in gas flow rate than oxygenators requiring upward flow. Still further, the present invention eliminates the need to increase the venous pressure to cause upward vertical venous blood flow against gravitational forces in order to operate the device as is necessary in all clinically used bubble oxygenators known to applicant.

These advantages, taken with the substantially increased efficiency of the present oxygenator in accomplishing gas transfer and heat exchange means that the oxygenator of the present invention gives better and safer blood oxygenation than has hitherto been available. In this regard, the rounded surfaces which define the travel path of the blood-gas mixture do not cause blood damage in the manner of sharp corners and thus also help to decrease the possibility of blood damage.

Other advantages, it is believed, of the present invention will be apparent to those skilled in the art. Thus, the present disclosure provides a description of the nature of the present invention and useful information with regard to its operational characteristics, and a statement of some of the advantages believed to be inherent therein.

What I claim is:

1. A method of oxygenating blood comprising the steps of:
    injecting oxygen-rich gas into liquid blood to form a blood-gas mixture having bubbles therein;
    causing said mixture to follow a generally downward path from the point of mixing until oxygenation has been substantially completed; and
    defoaming said mixture to remove bubbles therefrom.

2. The method of claim 1 wherein substantial rotational movement is imparted to at least a portion of said bubbles, said rotation being sufficient to effectively increase the amount of oxygenation of the blood.

3. The method of claim 1 wherein said mixture is caused to flow with a substantial absence of reverse flow.

4. The method of claim 1 wherein said mixture is subjected to a heat exchange step.

5. The method of claim 4 wherein said heat exchange comprises a filming heat exchange.

6. The method of claim 1 wherein, immediately after formation of said mixture, secondary flow is induced in said mixture.

7. The method of claim 1 wherein, prior to formation of said mixture, the flow direction of the incoming liquid blood is substantially perpendicular to the direction of said downward flow.

8. The method of claim 1 wherein at least a portion of the bubbles are caused to change shape from spherical to elongated ellipsoidal.

9. The method of claim 8 including the step of causing the shape of said ellipsoidal bubbles to change back to a spherical shape.

10. The method of claim 1 wherein said downward flow of said mixture comprises a combination of vertically downward flow and helically downward flow.

11. A method of oxygenating blood comprising the steps of:
    injecting oxygen-rich gas into liquid blood to form a blood-gas mixture having bubbles therein;
    causing said mixture to enter the upper end of a downwardly extending blood-oxygen mixing chamber;
    causing said mixture to follow a generally downward path from the point of mixing until oxygenation has been substantially completed;
    defoaming said mixture to remove bubbles therefrom; and
    removing oxygenated, liquid blood from said chamber.

12. The method of claim 11 wherein substantial rotational movement is imparted to at least a portion of said bubbles, said rotation being sufficient to effectively increase the amount of oxygenation of the blood.

13. The method of claim 11 wherein said mixture is caused to flow with a substantial absence of reverse flow.

14. The method of claim 11 wherein said mixture is subjected to a heat exchange step.

15. The method of claim 14 wherein said heat exchange comprises a filming heat exchange.

16. The method of claim 11 wherein, immediately after formation of said mixture, secondary flow is induced in said mixture.

17. The method of claim 11 wherein, prior to formation of said mixture, the flow direction of the incoming liquid blood is substantially perpendicular to the direction of said downward flow.

18. The method of claim 11 wherein at least a portion of the bubbles are caused to change shape from spherical to elongated ellipsoidal.

19. The method of claim 18 including the step of causing the shape of said ellipsoidal bubbles to change back to a spherical shape.

20. The method of claim 11 wherein said downward flow of said mixture comprises a combination of vertically downward flow and helically downward flow.

* * * * *